(12) United States Patent
Delisle

(10) Patent No.: US 6,955,893 B2
(45) Date of Patent: Oct. 18, 2005

(54) METHOD FOR PREVENTING SPOILAGE OF FOOD WITH BACTERIOPHAGE

(75) Inventor: Allan Delisle, Sykesville, MD (US)

(73) Assignee: University of Maryland, College Park, MD (US)

( * ) Notice: Subject to any disclaimer, the term of this patent is extended or adjusted under 35 U.S.C. 154(b) by 112 days.

(21) Appl. No.: 10/420,962

(22) Filed: Apr. 23, 2003

(65) Prior Publication Data

US 2004/0071636 A1 Apr. 15, 2004

Related U.S. Application Data

(60) Division of application No. 09/951,674, filed on Sep. 14, 2001, now Pat. No. 6,635,238, which is a continuation of application No. 08/886,119, filed on Jun. 30, 1997, now abandoned, which is a continuation-in-part of application No. 08/303,625, filed on Sep. 9, 1994, now abandoned.

(51) Int. Cl.[7] .................................................. C12P 1/00
(52) U.S. Cl. ........................ 435/41; 435/320.1; 435/200
(58) Field of Search .............................. 435/320.1, 441, 435/200, 325; 424/94.61, 234.1; 426/52, 56; 536/23.2

(56) References Cited

U.S. PATENT DOCUMENTS

| | | | | |
|---|---|---|---|---|
| 5,955,258 A | * | 9/1999 | Buist et al. | 435/4 |
| 6,335,012 B1 | * | 1/2002 | Fischetti et al. | 424/94.1 |
| 6,399,098 B1 | * | 6/2002 | Fischetti et al. | 424/464 |
| 6,451,365 B1 | * | 9/2002 | King et al. | 426/326 |
| 6,635,238 B2 | * | 10/2003 | Delisle | 424/49 |

OTHER PUBLICATIONS

Greer G. Inability of a Bacteriophage Pool to Control Beef Spoilage. Int J Food Micro 10(3–4)331–342, 1990.*
Delisle A. Bacteriophages of Psychrophilic Pseudomonads. Antonie van Leewenhoek 35(3)307–317, 1969.*

* cited by examiner

*Primary Examiner*—Ralph Gitomer (57) ABSTRACT

A method for the treatment and prevention of dental caries and periodontal diseases using bacteriophages and phage-encoded anti-bacterial enzymes to inhibit establishment of bacteria in the oral cavity is provided. Also provided are methods for studying the cell wall of an oral bacterium, a method for preventing spoilage of perishable items and a method for removing dextrans from surfaces utilized in sugar manufacture. Purified enzymes and the isolated DNA fragments encoding them are also provided.

1 Claim, 7 Drawing Sheets

METHOD FOR PREVENTING SPOILAGE OF FOOD WITH BACTERIOPHAGE

This application is a divisional application of Ser. No. 09/951,674 filed Sep. 14, 2001, now U.S. Pat. No. 6,635,238, which is a continuation application of Ser. No. 08/886,119 filed Jun. 30, 1997, now abandoned, which is a continuation in part application of Ser. No. 08/303,625 filed Sep. 9, 1994, now abandoned.

BACKGROUND OF THE INVENTION

1. Field of the Invention

This invention relates to bacteriophage-encoded enzymes useful in preventing dental caries and periodontal diseases. More specifically, this invention relates to lysozyme-like enzymes isolated from bacteriophages which are capable of killing cariogenic bacteria and other periodontal disease-causing organisms. The invention also relates to dextranase-like enzymes suitable for dental treatments (i.e., loosening plaque) and other applications where it is desired to remove dextran and other bacterial polysaccharides (i.e., mutan) synthesized from sucrose.

2. Description of the Related Art

Phages have been known to be present in the human mouth for many years (Meyers, C. E. et al (1958) *J. Dent. Res.* 37:175–178; Natkin, E. (1967) *Archs. Oral Biol.* 12:669–680; Shimizu, Y. (1968) *Odontology* 55:583–541) and have been isolated for several genera of oral bacteria, including oral enterococci (Natkin, E. (1967) *Archs. Oral Biol.* 12:669–680; Smyth, C. J. et al (1987) *J. Med. Microbiol.* 23:45–54), *Lactobacillus* sp. (Meyers, C. E. et al (1958) *J. Dent. Res.* 37:175–178; Stetter, K. O. (1977) *J. Virol.* 24:685–689; Tohyama, K. (1972) *Japan. J. Microb.* 16:385–395), *Veillonella* sp. (Shimizu, Y. (1968) *Odontology* (Japan) 55:583–541; Totsuka, N. (1976) *Bull. Tokyo Med. Dent. Univ.* 23:261–273), *Actinomyces* sp. (Bousque, J. L. et al (1988) *Ann. Mtg. IADR, J. Dent. Res.* 67:394. Abstr. No. 2253; Delisle, A. L. et al (1978) *Infect. Immun.* 20:303–306; Tylenda, C. A. et al (1985) *Infect. Immun.* 49:1–6), *Streptococcus mutans* and *S. sobrinus* (Armau, E. J. et al (1988) *Ann. Mtg. IADR, J. Dent. Res.* 67:121 Abstr. No. 69), *Actinobacillus actinomycetemcomitans* (Preus, H. R. et al (1987) *J. Clin. Periodontol.* 14: 245–247; Preus, H. R. et al (1987) *J. Clin. Periodontol.* 14: 605–609; Stevens, R. H. et al (1982) *Infect. Immun.* 35:343–349), *S. sanguis* (Parsons, C. L. et al (1972) *J. Biol.* 9:876–878; Parsons, C. L. et al (1973) *J. Bacteriol.* 113:1217–1222; Parsons, C. L. et al (1973) *J. Bacteriol.* 113:1505–1506), *Bacteroides buccalis* (Tylenda, C. A. et al (1987) *Absts. Ann. Mtg., Amer. Soc. Microb.*, #D-178, p. 101) and *Eikenella corrodens* (Williams, L. H. et al (1990) *Ann. Mtg., Amer. Soc. Microb.*, #D-61 p.90). They have even been observed in dental plaque by electron microscopy (Brady, J. M. et al (1977) *J. Dent. Res* 56:991–993; Halhoul, N. et al (1975) *Arch. Oral Biol.* 20:833–836). In spite of these reports, surprisingly little basic research has been done on oral phages, in view of their potential to affect bacterial populations in the oral cavity.

With regard to their function in dental plaque, phages are likely to influence the plaque flora in several potentially significant ways. Prophages, for example, provide immunity to super-infection by homoimmune phages and would presumably assist lysogens which carry them in competing with other bacteria in plaque by killing phage-sensitive competitors in a manner analogous to bacteriocinogenic cells. The semi-solid nature of dental plaque provides an especially favorable environment for this type of competition. Alternatively, lytic phage would be expected to select for phageresistant mutants of sensitive strains and for mucoid mutants (phenotypically phage-resistant), which could well have altered colonizing and pathogenic properties. Actinophage-resistant mutants have in fact already been used to study cell surface structures that appear to be involved in specific, intergeneric oral bacterial coaggregation reactions (Delisle, A. L. et al (1988) *Infect. Immun.* 56:54–59; Tylenda, C. A. et al (1985) *Infect. Immun.* 48:228–233), which are believed to play an important role in colonization of dental plaque (Kolenbrander, P. E. et al (1985) In, S. E. Murgenhagen and B. Rosan (eds) pp. 164–171, American Society for Microbiology, Washington, D.C.).

The literature on *S. mutans* phages dates back to 1970, when Greer first claimed to be able to induce phages, by treatment with mitomycin C, from oral streptococcal strains AHT, BHT and HHT (Greer, S. W., et al (1970) *IADR Abstr.* 160; *J. Dent. Res*, 48A:88) and subsequently claimed that the same virus was present in all of eight cariogenic streptococci he examined, but not in non-cariogenic strains (Greer, S. W., et al (1971) *J. Dent. Res.* 50:1594–1604). He then reported that lysogens could be cured of their prophages by treatment with acridine orange (Greer, S. W., et al (1971) IADR *Abstr.* 57: *J. Dent. Res.* 49:67) and nitrosoguanidine (Greer, S. W., et al (1972) *IADR Abstr.* 68: *J. Dent. Res.* 50:65). The latter was used to isolate temperature-sensitive mutants, one of which was heat-inducible and could be used to obtain cured cells by brief heating. Greer also proposed a curing procedure based on radiosensitization of DNA by incorporating 5-bromodeoxyuridine lysogens (Ramberg, E. et al (1973) *IADR Abstr.* 113: *J. Dent. Res.* 52a), but its application to *S. mutans* was never subsequently reported. Greer never reported the successful isolation of an infectious phage which could be grown in *S. mutans*. Difficulties in repeating Greer's induction experiments led many microbiologists to assume that he was really working with enterococci, which were common contaminants in the oral streptococcal cultures being exchanged among various laboratories during this time.

Feary was the next to report isolating phages for *S. mutans* (Feary, T. W. (1972) *IADR Abstr.* 67: *J. Dent. Res.* 50:65), from sewage, but all of his phage-sensitive strains were group D enterococci.

Klein and Frank also reported the presence of phages in cariogenic streptococci (and *Actinomyces*) (Klein et al (1973) *J. Biol. Buccale* 1:79–85), and later claimed that cured strains (isolated as survivors of heavy UV irradiation or treatment with acriflavine) of *S. mutans* OMZ 61 and 71 produced less extracellular insoluble polysaccharides from sucrose but were more cariogenic than their parent strains (Klein, J. P., et al (1975) *J. Biol. Buccale* 3:65–75). Unfortunately, their cultures were not studied by others and their results have not been confirmed. Like Greer, they did not isolate infectious phages which could grow in *S. mutans*.

Higuchi et al ((1977) *Infect. Immun.* 15:938–944) induced a phage out of "mucoid" *S. mutans* strain PK1 with mitomycin C and claimed that by using it to infect (or transfect) a rough, non-adherent mutant of this strain (which they believed to be a cured derivative) they could obtain transductants (and transfectants) that were mucoid, very adherent and contained the phage but which were also converted to an arg+ phenotype. The latter observation, since the parent strain was arg–, suggests that the transductants were really strains of *S. sanguis*; also their lysogenic culture, PK1, is an unusual strain which most workers now believe is not *S.*

*mutans*. These authors reported that transfection of *S. sanguis* 10556 with phage PK1 DNA yielded mucoid, adherent mutants which produced large amounts of levan (Higuchi, M. et al (1977) *Infect. Immun*. 15:945–949). These colonies have the appearance of typical *S. salivarius* colonies; also, since they were arg– (which is characteristic of *S. salivarius*), whereas the parent strain (10556) was arg+, the validity of the results is very questionable.

Upon reviewing the literature on *S. mutans* phages, the existence of such phages has not been confirmed, except in the case of lytic phages isolated by Armau (Armau et al (1988) *Ann. Mtg. IADR, J. Dent. Res*. 67:121, Abstr. No. 69). Armau isolated 23 *S. mutans* phages from 3,974 dental plaque samples, using 17 test host strains. Nine were isolated on three serotype c strains, nine on one serotype e strain, one on the serotype f strain and four on two serotype d strains. No phages were isolated for one serotype b strain or two serotype g strains tested. All of the phages proved to serotype-specific. Four of the phages plated with reduced efficiency on different strains of the same serotype, suggesting the presence of restriction/modification systems.

Prior art methods for combatting the oral bacteria which lead to dental caries have relied on physical or chemical treatments to remove plaque or kill microorganisms, in a non-specific manner. Desirable organisms were therefore removed along with the target organisms. In the case of antibiotic treatments, resistant mutants often developed, rendering further treatment ineffective.

Current treatments which claim to reduce the numbers of organisms in dental plaque include a number of mouthwashes (rinses) that contain a variety of bacteriostatic and bacteriocidal organic chemicals. These chemicals include phenols, alcohols, peroxides, detergents/surfactants, quaternary ammonium compounds, root extracts (sanguinarine) and fluorides. A mouthrinse containing the bis-biguanide antibiotic chlorhexidine is now available, by prescription only, in the U.S. With the exception of fluorides and chlorhexidine, none of the currently available oral health care products have been demonstrated to be highly therapeutically effective in reducing plaque or preventing caries.

Therefore, in view of the aforementioned deficiencies attendant with prior art methods of treating and preventing dental caries and periodontal diseases, it should be apparent that there still exists a need in the art for a method of effectively combatting the oral bacteria which lead to these conditions.

SUMMARY OF THE INVENTION

In contrast to prior art methods of treating and preventing dental caries and periodontal diseases, the phage-encoded enzymes of the present invention do not lead to development of resistant bacterial mutants, because their development in response to the present compositions would require too drastic an alteration in the basic structure of the bacterial cell wall.

Accordingly, a major object of the present invention is to provide a method for the treatment and prevention of dental caries and periodontal diseases using phage-encoded anti-bacterial enzymes to kill the organisms causing these diseases in the oral cavity.

Another object of the present invention is to provide a method for studying the cell wall of an oral bacterium by treating the bacterium with a phage-encoded enzyme which degrades the cell wall.

A further object of the present invention is to provide a method for preventing spoilage of fresh, refrigerated or pasteurized perishable items by treating these items with a phage-encoded anti-bacterial enzyme which inhibits growth of a gram-positive spoilage bacterium on the items.

Another object is to provide a method for the removal of insoluble dextran polysaccharides by treating with a phage-encoded enzyme.

A still further object of the present invention is to provide a method for the removal of dental plaque by treating the oral cavity with a phage-encoded enzyme.

A still further object of the present invention is to provide an isolated and purified phage-encoded anti-bacterial enzyme which inhibits the establishment of an oral bacterium.

Another object of the present invention is to provide an isolated and purified phage-encoded enzyme which can be used to remove insoluble dextran polysaccharides.

Yet another object of the present invention is to provide an isolated and purified phage-encoded enzyme which can be used to remove dental plaque.

Another object of the present invention is to provide DNA fragments isolated from bacteriophage which encode the enzymes of the present invention.

A further object of the present invention is to provide an expression vector containing the DNA fragments encoding the enzymes of the present invention.

A still further object of the present invention is to provide a host cell containing an expression vector including DNA fragments encoding the enzymes of the present invention.

Another object of the present invention is to provide antibodies to the enzymes of the present invention.

A still further object of the present invention is to provide vehicles for supplying and treating with the enzymes of the present invention.

Yet another object of the present invention is to provide a genetically engineered non-cariogenic organism which produces phage-encoded enzymes that inhibit the establishment of a cariogenic organism.

With the foregoing and other objects, advantages and features of the invention that will become hereinafter apparent, the nature of the invention may be more clearly understood by reference to the following detailed description of the preferred embodiments of the invention and to the appended claims.

DETAILED DESCRIPTION OF THE PREFERRED EMBODIMENTS OF THE INVENTION

More particularly, the present invention relates to the discovery and use of a family of bacteriolytic enzymes encoded on the genome(s) of bacterial viruses (bacteriophages) which infect the oral bacteria that are thought to be the etiological agents of dental caries and periodontal diseases. Specifically, this invention covers the source, production and use of phage-encoded, lysozyme-like enzymes in topical treatment preparations to kill (a) cariogenic bacteria on tooth surfaces, and (b) periodontal disease organisms in periodontal pockets, in order to halt their destructive effects. Such enzymes can thus be used to both treat and prevent dental diseases.

Other applications of these lysozyme-like enzymes include cleaning or disinfecting of dental appliances, including fixed and removable bridges, partial and full dentures, caps and crowns; veterinary applications; orthodontic and surgical appliances; implant materials; temporary crowns, caps and bridges; endodontic uses (root canals); periodontal treatments (root scaling, cleaning); preparation of enamel, dentinal and cemental surfaces for restorations.

The invention also relates to phage-encoded dextranase enzymes which can be used for dental application such as removing plaque. In addition, these enzymes may be utilized in non-dental applications, such as in industrial sugar processing and refining operations in which sugar is stored, transported or pumped as liquid solutions. Bacterial contamination of such solutions is common, which results in increased viscosity of the solutions, clogged pipes, valves, etc., due to the insoluble dextran polysaccharides synthesized by the bacteria. Removal of these dextran polysaccharides can be accomplished by addition of dextranase enzymes. Similar treatments might be useful in many other types of food processing operations involving liquid sucrose (i.e., sugar solutions).

In order to colonize, survive and grow in dental plaque, cariogenic streptococci apparently evolved their unique combination of phenotypic properties, namely the ability to produce special adherent extracellular polysaccharides (EPS) from sucrose, to be resistant to salivary lysozyme, and to tolerate the high acid conditions in this econiche. Phages which infect these organisms also had to evolve in order to grow in this environment, and in so doing acquired new, possibly unique, mechanisms to efficiently adsorb to and lyse their host cells, even at low pH.

That the phages produce lysozyme-like enzymes is suggested by the finding that growth of a phage in a bacterial broth culture results in complete lysis; after 1–2 hr. there is no visible evidence of cellular debris, indicating nearly complete dissolution of host cell walls. Further, phage-resistant mutants and non-homologous strains of *S. mutans*, to which the phages cannot adsorb, are lysed when lysate is spotted onto freshly poured top agar lawns of these cells. Since the phage cannot adsorb to the cells they cannot cause infection, lysis-from-without, or induce an autolytic response.

Considerable difficulty has in fact been experienced in isolating phage-resistant mutants, due to the presence of lytic enzyme(s) in phage lysates. Unless lysates are diluted $10^2$ to $10^3$, no surviving colonies appear in top agar lawns of sensitive hosts plated with 0.1 ml of phage suspension.

Furthermore, non-growing, stationary-phase cells of *S. mutans* plated in 1% agarose are lysed by the enzymes present in phage lysates. Under the conditions used, the phages present cannot diffuse into the agarose to adsorb to or infect the cells. Since the cells are starved and essentially non-viable, the lysis cannot be an autolytic response; zones develop at room temperature and in the presence of $Na_3N$ so no growth can occur.

Since the phage can grow normally in high acid conditions (low pH), their lysozymes are unique in this property, animal lysozymes being virtually inactive at low pH. The lytic enzymes of the present invention are active at low pH, and thus are effective under the conditions which exist in vivo in dental plaque. This is significant since bacteria which inhabit dental plaque are quite resistant to animal lysozymes under these conditions.

Also, because of their high activity under conditions of low pH, another use of the antibacterial, lytic enzymes described in this invention is their inclusion in food products and other perishable commodities to prevent bacterial spoilage. These enzymes are more active, and therefore more effective, in acid foods such as cheeses than chicken lysozyme, which has been used for this purpose. Thus, the use of the present enzymes in acid foods to prevent spoilage should, therefore, function much better than presently available commercial lysozyme preparations.

The present invention also includes phage-encoded dextranase enzymes. This enzymatic activity has been found to be present in phage lysates by spotting onto Blue dextran agar plates (0.1%, w/v). This method is relatively sensitive and in fact has been used to detect the expression of *S. mutans* dextranase in *E. coli* (F. Barrett, Jr., T. A. Barrett and R. Curtiss, III (1987) *Infect. Immun.* 55:792–802; R. A. Burne, B. Rubinfeld, W. H. Bowen and R. E. Yasbin (1986) *J. Dent. Res.* 65:1392–1401; W. A. Jacobs, J. F. Barrett, J. E. Clark-Curtiss and R. Curtiss III (1986) *Infect. Immun.* 52:101–109).

The phage glucan-degrading enzymes of the present invention degrade dextran and the caries-related EPSs of the cariogenic streptococci that constitute the major components of dental plaque. The phage enzymes enable the phage to infect host bacteria even when the bacteria are grown in the presence of sucrose, which results in their synthesis of large amounts of soluble and insoluble extracellular polysaccharides (EPSs). Thus, EPS-depolymerizing enzymes could be effectively used to remove this material from teeth.

The present invention includes anti-caries products incorporating either whole, infectious phages or the appropriate, purified phage-encoded enzymes. Treatments involving whole, infectious phage have the advantage of providing a highly specific, long term biological mechanism for controlling cariogenic bacteria. Once intact phage colonize the plaque, they should survive for considerable periods of time, attacking sensitive cells as they arise, and maintaining their number at low, non-cariogenic levels.

In addition, the enzymes of the present invention, being proteins, adhere to dental plaque well, and so act over considerable periods of time. Continued, intermittent applications of these enzymes can then be used to prevent the re-establishment of these bacteria in the oral cavity.

Vehicles for the enzymes can include mouthwashes/rinses, topical gels/ointments, toothpastes/powders, slow release implants/coatings, chewing gums and the like. Application of phage-encoded enzymes facilitates plaque removal both in the home and in the dentist's office. Physical removal of dental plaque can be carried out using any known topical means, including dental floss, toothpaste (including abrasive toothpastes), plaque-loosening mouthwashes and professional cleaning by a dentist or dental hygienist. Other preventive measures include pit and fissure sealants (for children) and various fluoride-containing toothpastes and gels (to reduce the acid-solubility of enamel).

Phage lysates (preparations obtained by growing phage on a susceptible host in broth culture), which contain unpurified lytic enzymes in relatively dilute concentrations, degrade the cell walls of (and thus kill) certain gram-positive bacteria found in dental plaque. This is observed with phages of *Actinomyces* and of *Streptococcus mutans*. Purified enzymes of the type described can also be used as research tools to lyse pure cultures of lysozyme-resistant, oral bacteria and to study their unique cell wall structures.

The enzymes (or infectious phage) on which this invention is based are "natural" products, having been isolated from human mouths initially and therefore do not have any harmful effect on oral tissues. Chicken lysozyme is presently given GRAS status (generally recognized as safe) by the FDA for use in food products. Ingestion of phage lysozymes would therefore be harmless. Being proteins, they should be readily degraded by normal digestive enzymes, and thus should not harm tissues or beneficial microorganisms in the gastrointestinal tract.

Since phage-encoded enzymes are not normally synthesized in large amounts during phage growth, cloning their genes into appropriate vectors allows these enzymes to be produced in large quantities for purification. This invention therefore includes the construction and use of such recombinant DNA vectors and their appropriate hosts.

Additional embodiments of this invention include genetically engineered, non-cariogenic organisms (such as *S. sanguis*) which can colonize dental plaque but produce phage-encoded enzymes that inhibit establishment of *S. mutans*. Such engineered "replacement therapy" strains would provide long-term protection against dental caries.

This approach, described by Hillman & Socransky (Replacement therapy for the prevention of dental disease, *Adv. Dent Res* 1(1):119–125, 1987) employs implanting a non-cariogenic organism (in this case a mutant of *S. mutans* which cannot produce lactic acid, which causes caries) into a normal mouth to replace resident, wild type strains of *S. mutans*. This "effector" strain, if it can out-compete the resident strains, for example by producing a bacteriocin, replaces them and caries can no longer occur because there is not enough acid to dissolve the tooth enamel. Since bacteriocin-resistant mutants of *S. mutans* are likely to occur (like phage-resistant mutants) long term protection could not be guaranteed because such mutants would not be inhibited by the effector strain. This invention could be used to develop effector strains of *S. sanguis*, which is the best colonizer of teeth and is non-cariogenic. By introducing phage lysozyme genes which code for enzymes that lyse *S. mutans* (but not *S. sanguis*) into *S. sanguis* in such a way that they are continuously expressed at low levels, an effector strain could be obtained which would prevent establishment by cariogenic *S. mutans*. This situation would persist indefinitely since *S. mutans* do not appear to be capable of developing resistance to lysozyme by simple mutation.

Target cariogenic or periodonto-pathogenic bacteria may be from the genera *Actinobacillus, Actinomyces, Bacteroides, Capnocytophaga, Eikenella, Eubacterium, Fusobacterium, Haemophilus, Lactobacillus, Peptostreptococcus, Porphyromonas, Prevotella, Rothia, Selenomonas, Streptococcus, Treponema, Wolinella*.

At the present time antibacterial phage lysozymes can be demonstrated to be produced by bacteriophages which infect the following gram-positive, caries-related species: *Actinomyces viscosus, A. naeslundii* and *Streptococcus mutans*. For use in the present invention, phage specific for any *S. mutans* strain are preferable, and phage for serotype c, e or f strains are most preferable.

Phages have also been isolated for *S. sobrinus* and *Lactobacillus casei*, two other organisms considered to be involved in dental caries, and analogous enzymes are presumed to be coded in the genomes of these phages. Recent studies with certain gram-negative organisms involved in periodontal diseases also indicate that phages exist for these organisms as well, suggesting that phage-encoded enzymes which can lyse them are likely to also exist. Thus, phage isolated from these organisms are also contemplated by the present invention.

Furthermore, the sources of the enzymes which form the basis of this invention are not limited to the oral bacteriophages isolated to date, but should include any additional bacterial viruses, including those of other bacterial species, which may be discovered in the future.

Host strains are grown in nutrient broth appropriate for the particular species and strain utilized. A preferable broth for *S. mutans* is TYNP broth.

Phage are isolated from the host strain by any manner known in the art, including isolation from nutrient broth, or from lysed cells on agar plates. Most preferably, phage are isolated from the host bacteria from overnight confluent lysis top agarose plates. Phage suspensions are treated with nucleases and precipitated by any known means, preferably using polyethylene glycol (PEG). Phage are isolated by centrifugation of the phage-precipitant solutions, followed by density gradient centrifugation or by sedimentation.

The resulting isolated phages are tested to determine host susceptibility, usually by production of clear plaques on top agarose. Phage titers are determined by counting the number of plaques formed at a particular dilution of phage. The phage can be examined using electron microscopy to study their size and morphology.

To confirm the identity and composition of the phage isolated by the above procedures, phage structural proteins are examined by disrupting the phage by boiling in SDS+ β-ME and electrophoresing lysate proteins on an acrylamide gel. Western blots may be used to identify particular proteins, and the presence or absence of certain proteins may be determined using immunological assays such as enzyme-linked immunosorbant assays (ELISA), radioimmune assays, and the like.

Once purified solutions of the enzymes are obtained, one can also examine the DNA structures of and genetic relationships among *S. mutans* phages by cloning the genes encoding these enzymes.

Phage DNA can be isolated by methods well known in the art, including methods described by Delisle et al (*Infect. Immun*. 56:54–59, 1988), the contents of which are hereby incorporated by reference. Other useful methods are included in Sambrook et al (1989, *Molecular Cloning. A Laboratory Manual*, 2nd ed. Cold Spring Harbor Lab. Press. N.Y. 3 vols.), the contents of which are hereby incorporated by reference.

The isolated DNA is analyzed by any means known in the art, including electron microscopy, Southern blots, restriction enzyme analysis and electrophoresis to determine relative mobilities, and the like. Particular DNA fragments, i.e., those which contain the genes of interest, or fragments thereof, can be isolated by restriction digestion, and elution from agarose gels, or by chromatographic methods.

By digesting the ends of the DNA fragment with the same enzyme or a similarly cutting enzyme as that used to digest a particular cloning vector, the DNA fragment of interest can be inserted into an appropriate cloning vector. Alternatively, DNA fragments and vectors may be blunt-ended with Klenow fragment or with mung bean nuclease. DNA sequences from each phage can be cloned into the appropriate plasmid and phage vectors, using standard recombinant DNA techniques, in order to isolate phage genes which code for the following proteins of interest: (a) lysozymes; (b) other cell wall lysins; (c) dextranases; (d) depolymerases active against other extracellular polysaccharides synthesized by their hosts from sucrose (mutan); and (e) the receptor site adsorption proteins which determine serotype-specificity. Cloning vectors of interest include any known in the art, such as pBS, pUC and M13-based plasmids for sequencing, pBR322-based plasmids and phage (such as λgt10) and expression vectors, such as λgt11 and the like.

The presence of phage-encoded genes in recombinant clones of E. coli or other suitable hosts can be detected using phage enzyme gene-specific probes, by detecting expression of appropriate lytic/depolymerase activities or phage structural proteins, and by complementation of lysozyme-defective mutants of E. coli phages.

The cloned fragments can then be sequenced, and phage-specific oligonucleotide probes designed for other purposes, including PCR amplification, site-directed mutagenesis, and isolation of related sequences. In this regard, the invention also relates to phage-encoded enzymes which contain mutations which call on the proteins to substantially retain their enzymatic activity. In addition, the phage-encoded enzymes may be specifically engineered to contain mutations which increase or alter their activity or characteristics in a desired manner.

The cloned fragments can then be inserted into replicable expression vectors which comprise a nucleic acid encoding the subject gene, i.e., the coding sequence is operably linked to a nucleotide sequence element capable of effecting expression of the phage-encoded enzyme. In particular, the nucleotide sequence elements can be a promoter, a transcription enhancer element, a termination signal, a translation signal, or a combination of two or more of these elements, generally including at least a promoter element.

Replicable expression vectors are generally DNA molecules engineered for controlled expression of a desired gene, especially where it is desirable to produce large quantities of a particular gene product, or polypeptide. The vectors comprise one or more nucleotide sequences operably linked to a gene to control expression of that gene, the gene being expressed, and an origin of replication which is operable in the contemplated host. Preferably the vector encodes a selectable marker, for example, antibiotic resistance. Replicable expression vectors can be plasmids, bacteriophages, cosmids and viruses. Any expression vector comprising RNA is also contemplated.

The replicable expression vectors of this invention can express phage-encoded enzyme at high levels. These vectors are preferably derived from a prokaryote.

Prokaryotic vectors include bacterial plasmids and bacteriophage vectors that can transform or infect such hosts as E. coli, B. subtilis, Streptomyces sps. and other microorganisms. Many of these vectors are based on pBR322, M13 and lambda and are well known in the art and employ such promoters as trp, lac, $P_L$, T7 polymerase and the like. The cells which serve as hosts for these vectors are well known in the art and a suitable host for a particular vector can be readily selected by one of ordinary skill in the art. Numerous texts on recombinant DNA techniques are available which describe expression vectors, the control sequences contained therein, and general methodology for making expression constructs. Hence, one skilled in the art has available many choices of replicable expression vectors, compatible hosts, and well-known methods for making and using the vectors.

Another aspect of this invention provides a homogenous protein encoded by the subject phage-encoded genes. Moreover, peptides and fragments as well as chemically modified derivatives of this protein are also contemplated.

Purification of the subject phage-encoded proteins from natural or recombinant sources can be accomplished by conventional purification means such as ammonium sulfate precipitation, gel filtration chromatography, ion exchange chromatography, adsorption chromatography, affinity chromatography, chromatafocusing, HPLC, FPLC, and the like. Where appropriate, purification steps can be done in batch or in columns. Fractions containing the phage-encoded enzyme are identified by enzymatic activity.

Peptide fragments can be prepared by proteolysis or by chemical degradation. Typical proteolytic enzymes are trypsin, chymotrypsin, V8 protease, subtilisin and the like; the enzymes are commercially available, and protocols for performing proteolytic digests are well known. Peptide fragments are purified by conventional means, as described above. Peptide fragments can often be identified by amino acid composition or sequence. Peptide fragments are useful as immunogens to obtain antibodies against the subject phage-encoded enzyme.

The present invention also relates to antibodies to the subject phage-encoded enzymes. Such antibodies may be monoclonal or polyclonal and are contemplated to be useful in developing detection assays (immunoassays) for proteins, monitoring the activity of the phage-encoded enzyme and in purifying the phage-encoded enzyme. Thus, in accordance with this invention, an antibody to a phage-encoded enzyme encompasses monoclonal or polyclonal antibodies or to antigenic parts thereof.

Both polyclonal and monoclonal antibodies are obtainable by immunization of an animal with purified enzyme, purified recombinant enzyme, fragments of these proteins, or purified fusion proteins of the enzyme with another protein. In the case of monoclonal antibodies, partially purified proteins or fragments may serve as immunogens. The methods of obtaining both types of antibodies are well known in the art with excellent protocols for antibody production being found in Harlow et al. (1988) *Antibodies: A Laboratory Manual*, Cold Spring Harbor Laboratory, Cold Spring Harbor, N.Y., 726 pp.

Polyclonal sera are relatively easily prepared by injection of a suitable laboratory animal with an effective amount of the purified enzyme, or parts thereof, collecting serum from the animal, and isolating specific sera by any of the known immunoadsorbent techniques. Antibodies produced by this method are useful in virtually any type of immunoassay.

Monoclonal antibodies are particularly useful because they can be produced in large quantities and with a high degree of homogeneity. Hybridoma cell lines which produce monoclonal antibodies are prepared by fusing an immortal cell line with lymphocytes sensitized against the immunogenic preparation and is done by techniques which are well known to those who are skilled in the art. (See, for example, Douillard, I. Y. and Hoffman, T., "Basic Facts About Hybridomas", in *Compendium of Immunology*, Vol. II, L. Schwartz (Ed.) (1981); Kohler, G. and Milstein, C., *Nature* 256: 495–497 (1975) and *European Journal of Immunology* 6: 511–519 (1976); Harlow et al.; Koprowski, et al., U.S. Pat. No. 4,172,124; Koprowski et al., U.S. Pat. No. 4,196,265 and Wands, U.S. Pat. No. 4,271,145, the teachings of which are herein incorporated by reference.

The genes coding for the enzymes of the present invention can also be cloned into other organisms to facilitate and improve the production and purity of their respective enzymes by a variety of genetic engineering techniques. Protein engineering techniques are then employed to modify the properties of these enzymes, for example to improve their stability, i.e. at low pH.

The following examples are presented in order to more fully illustrate the preferred embodiments of the invention. They should in no way be construed, however, as limiting the broad scope of the invention.

EXAMPLE 1

Characterization of *S. mutans* Phages

Bacteriophages and host strains. The following 3 *S. mutans* phages (and their respective host strains) were utilized: Phage M102, host strain P42; Phage e10, host strain LM7; and Phage f1, host strain OMZ 175 (E. Armau, J. L. Bousque, D. Boue and G. Tiraby (1988) *Ann. Mtg. IADR, J. Dent. Res.* 67:121 Abstr. No. 69). Strains of other serotypes (a, b, d, g, h) and related species of the mutans group might also be used. *Bacillus* phage Φ29 and several *Actinomyces* phages were also used for comparative purposes.

Growth and purification of phases. Each of the above host strains were grown in TYNP broth, which is composed of 30 g/l Trypticase Soy Broth (BBL Labs), 5 g/l yeast extract, 5 g/l neopeptone (Difco) and 5 g/l $K_2HPO_4$. Phage stocks were prepared either by harvesting phage from overnight confluent lysis top agarose plates, using 5 ml of SM buffer (100 mM NaCl, 50 mM Tris, 10 mM $MgSO_4.7H_2O$, 0.01% gelatin; pH 7.5) per plate, or by infecting log-phase cells ($A_{660}$=0.4) at a multiplicity of infection (MOI) of about 0.1 and incubating several hours at 37° C. The resulting suspensions were first treated with RNase and DNase (1 82 g/ml each) for 1 hr at 37° C. and then centrifuged at low speed to remove whole cells and debris. NaCl was added to 1M, followed by polyethylene glycol 8000 (PEG) to 10% (w/v) and the suspensions were stored in the cold overnight. Phage-PEG aggregates were centrifuged at 8,000×g for 30 min and the pellets resuspended in 1/100 vol of SM buffer. The PEG-phage concentrates were either diluted and used to sediment phage directly or first extracted with $CHCl_3$ to remove PEG. Phage were purified by isopycnic CsCl density gradient centrifugation or by sedimentation through glycerol step gradients, depending on the degree of purity required. For the latter, phage suspensions were overlaid onto two-step gradients, composed of 40% glycerol and 10% glycerol (in SM) and centrifuged at 4° C. for 1 hr at 30,000 rpm (SW41 rotor). Phage pellets from glycerol step gradients were then resuspended in a small volume of SM and used to prepare phage DNA. Phage bands from CsCl gradients were collected and recentrifuged in CsCl for 68 hr at 4° C. (33,000 rpm, SW41 rotor) to obtain high purity preparations.

The results in Table 1 were obtained with phages M102, e10 and f1, which infect certain strains of serotype c, e and f of *S. mutans*. It is generally accepted that serotype c, e and f strains of *S. mutans* are the primary and most common etiologic agents of human dental caries (>90% being serotype c). Therefore, use of the 3 phages currently available yield data which should be relevant to most phages of cariogenic streptococci.

TABLE 1

| *S. mutans* bacteriophages and host strains | | | |
|---|---|---|---|
| Phage | Isolation Host | Host Serotype | Other Sensitive Strains |
| M102 | P42 | c | UA174 |
| e10 | LM7 | e | P4, B14 |
| f1 | OMZ 175 | f | JH 34 |

Figure 1:
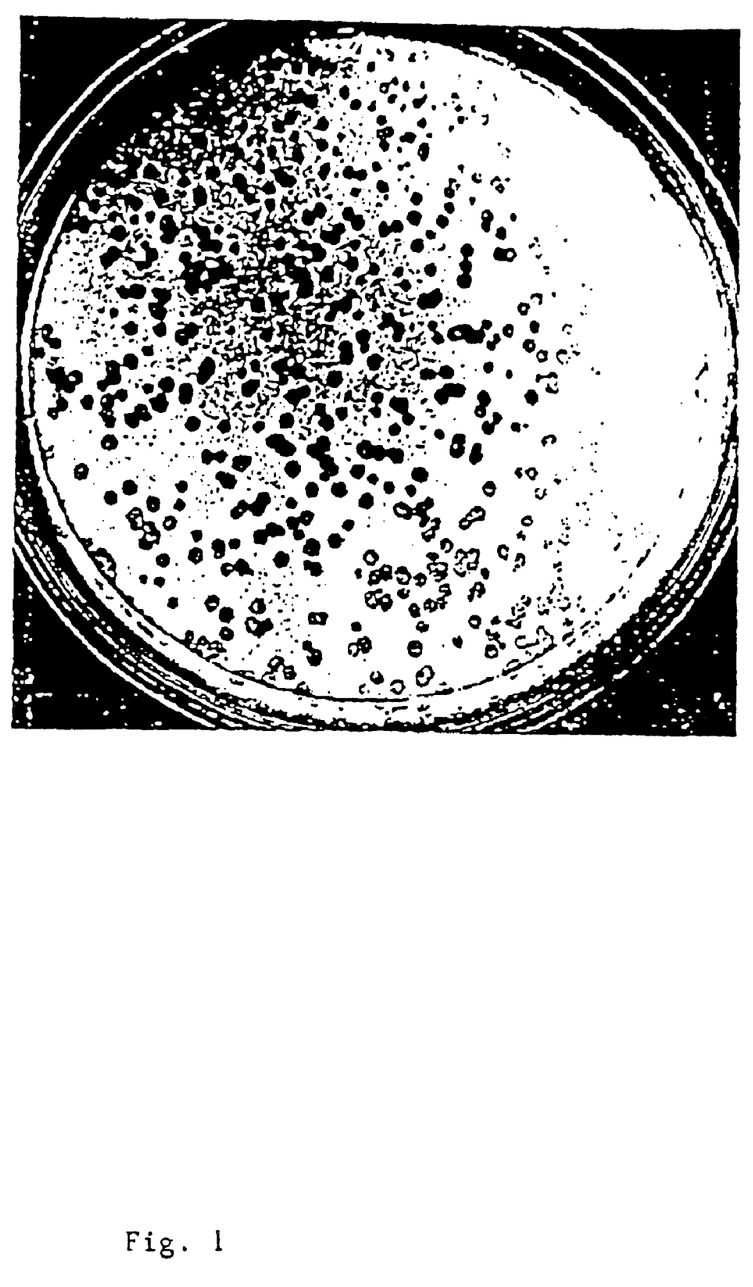
FIG. 1 shows plaques of phage M102 on *S. mutans* P42.

Preliminary studies with the 3 viruses can be summarized as follows. Each phage produced clear plaques, which vary in size from 2–4 mm (FIG. 1). They grew in normal media and do not require MOPS-buffered medium. Each phage appeared to be strictly lytic, showing no obvious evidence of turbid areas containing lysogenized cells, and easily grew in broth lysates to high titers ($10^{10}$–$10^{11}$ pfu/ml).

Figure 3:
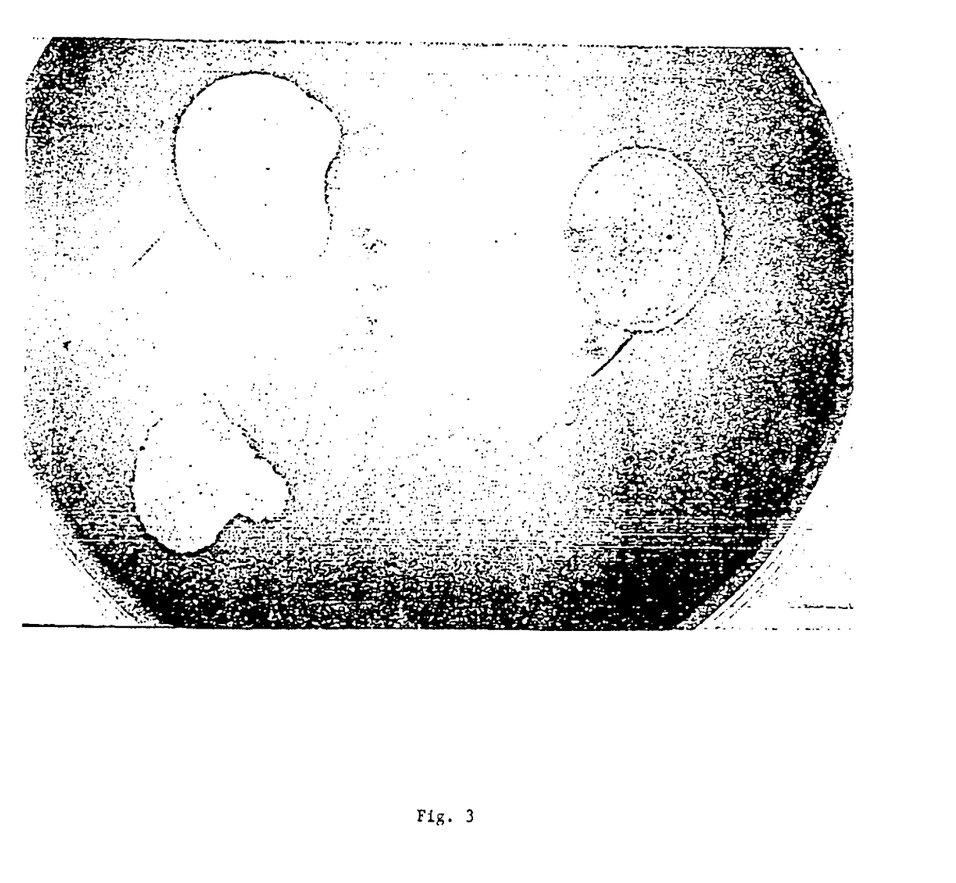
FIG. 3. shows lysis zones and plaque formation by phage M102 on host *S. mutans* P42 plated on Mitis-Salivarius agar. 25 µl of undiluted phage suspension and $10^{-2}$, $10^{-4}$ and $10^{-6}$ dilutions were spotted onto top agar layer (½ strength Mitis-Salivarius agar) before incubation.

Phage adsorption and growth was not prevented in sucrose-containing media (FIG. 3). The clear zones in sucrose-containing agar overlays continued to increase in size somewhat on prolonged incubation, and their edges changed, suggesting that EPSs were being degraded. Plaque formation was also not inhibited by the presence of human saliva, when tested as described previously with *Actinomyces viscosus* phage Av-1 (Delisle, A. L. 1986 Growth of *Actinomyces viscosus* bacteriophage Av-1 in the presence of serum, saliva and dental plaque. *Microbiol. Lett.* 33:107–113).

Each phage produced plaques only on some strains of a single serotype. In the case of M102, 6 of 19 fresh clinical *S. mutans* isolates (picked from MS-bacitracin agar) were sensitive to this phage, but none were sensitive to e10 or f1, which attack only serotype e and f strains, respectively. Since the majority of these isolates were presumed to be c serotypes, the reason for the lack of plaque formation by M02 on the other strains is unknown. Phage-resistant mutants occur with normally-expected frequency, which may be pertinent to this point. Preliminary experiments confirmed that each phage was serotype-specific, that is they did not adsorb to host cells of either of the other 2 serotypes, nor to serotype d/g strains of *S. sobrinus*. These results were obtained by mixing phage with non-sensitive hosts, centrifuging and titering the number of free phage before and after exposure to the test host.

Figure 4:
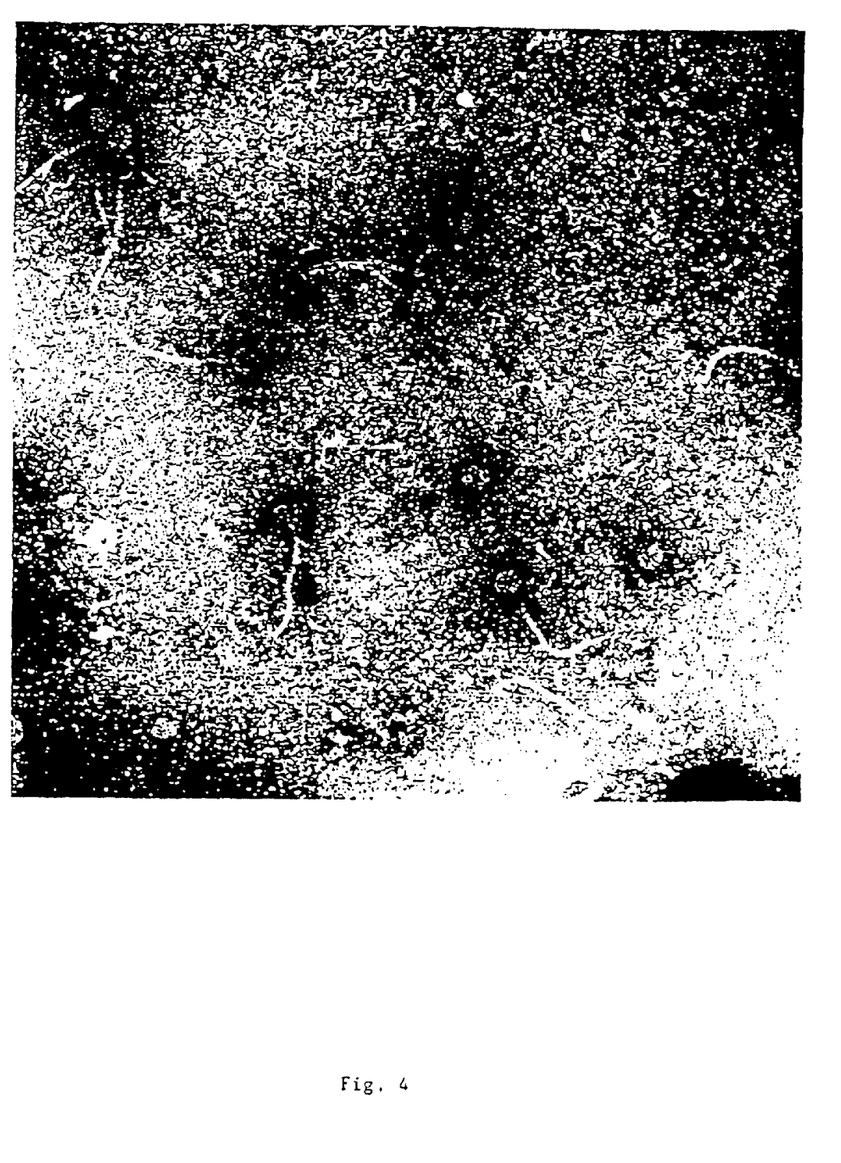
FIG. 4 is an electron micrograph of phage f1, negatively stained with 1% phosphotungstate; 40,000×.

Electron microscopy of the phages revealed that each was the same type and size virion. They belong to Bradley's morphotype B, having a polyhedral head and long, non-contractile tails (FIG. 4). The size of each phage virion is listed in Table 2. The morphology of these phages differed from those shown in electron micrographs of *S. mutans* phages published by several earlier workers (Greer, S. B., W. Hsiang, G. Musil and D. D. Zinner (1971) Viruses of cariogenic streptococci, *J. Dent. Res.* 50:1594–1604; Higuchi, M., G. H. Rhee, S. Araya and M. Higuchi (1977a) Bacteriophage deoxyribonucleic acid-induced mutation of *Streptococcus mutans, Infect. Immun.* 15:938–944; Klein, J. P. and R. M. Frank (1973) Mise en evidence de virus dans les bacterie cariogenes de la plaque dentaire, *J. Biol. Buccale* 1:79–85).

TABLE 2

Size of phage virions

| Phage | Head[1] | Tail Length | Tail Width |
|---|---|---|---|
| M102 | 67 nm ± 0.4 | 283 nm ± 4 | 8.3 nm ± 0.1 |
| f1 | 68 nm ± 0.4 | 286 nm ± 6 | 8.3 nm ± 0.1 |
| e10 | 68 rim ± 0.4 | 287 nm ± 10 | 8.3 nm ± 0.1 |

[1]Distance between parallel faces

EXAMPLE 2

Experiments with Phase Lysates

Figure 2:
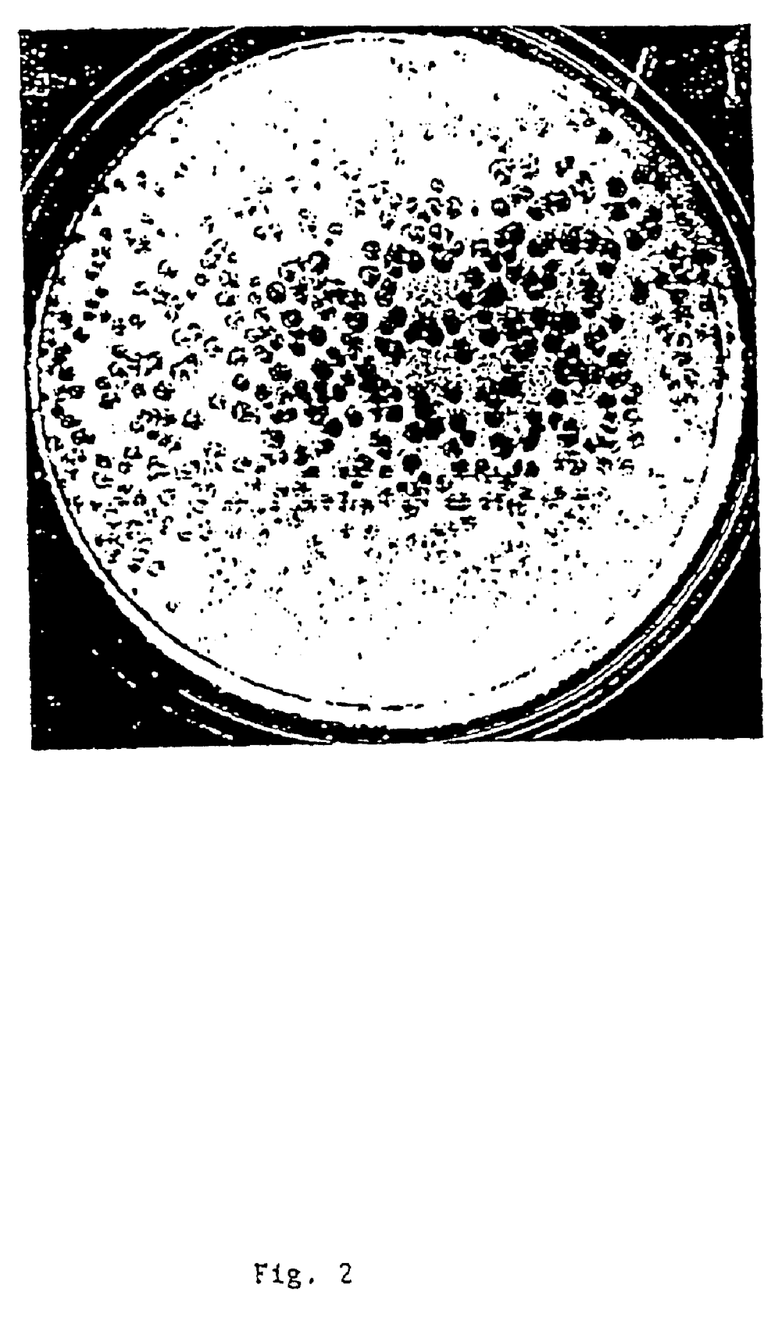
FIG. 2 shows plaques of phage f1-turbid on *S. mutans* OMZ175.

Lysates of each phage, obtained by infecting a growing broth culture of sensitive cells, diluted even to $10^{-2}$ to $10^{-3}$ caused clear zones (indicating cell lysis) when spotted onto overlays of all three serotype strains of S. mutans, even those on which the phage cannot form plaques. Phage-resistant mutants were also lysed, indicating that such zones are not due to lysis-from-without, whereas gram-negative cells and cells of unrelated gram-positive organizations were not lysed. Taken together, these observations indicate that each phage produced a potent lysozyme-like enzyme which was relatively specific for S. mutans. While each of the three phages produced clear plaques on its respective host, in each case a turbid-plaque forming variant of each phage was readily isolated; an example is shown in FIG. 2.

EXAMPLE 3

Analysis of Phase Proteins

The size and number of structural proteins of each phage is determined by SDS-PAGE of SDS-β-meOH-boiled whole phage, using standard 10% Laemmli gels. Western blots are used with the antisera produced below to determine which proteins are antibody-detectable. Gel-separated proteins are transferred to nitrocellulose membranes, using a Bio-Rad Trans-Blot apparatus, reacted with antiphage serum and then detected with commercially obtained horseradish peroxidase-conjugated anti-rabbit IgG antibodies.

5–10 major proteins are detected in each phage, with the most abundant in each case being tail subunits (due to the very large size of the phage tails). If it becomes necessary to determine the location of certain proteins in the intact phage, chemical treatments can be used to separate various phage components, e.g., heads and tails, and these can be identified by electron microscopy.

In some electron micrographs, a thin fiber extending from the tip of each phage tail can be observed. These are thought to be protein and not DNA since they have been observed in DNase-treated lysates. By analogy to phage lambda, it seems likely that this fiber is the adsorption apparatus of the phage.

EXAMPLE 4

Preparation of Phage DNA

Phage DNAs were isolated from purified phage by treatment with Proteinase K in the presence of EDTA and SDS, extracting with phenol and $CHCl_3$ and then precipitated with ammonium acetate and ethanol, as described previously for Actinomyces phages (A. L. Delisle, J. A. Donkersloot, P. E. Kolenbrander and C. A. Tylenda (1988) Infect. Immun. 56:54–59).

Many of the methods utilized protocols given in Sambrook et al (J. Sambrook, E. F. Fritsch and T. Maniatis (1989) Molecular Cloning. A Laboratory Manual, 2nd ed. Cold Spring Harbor Lab. Press. N.Y. 3 vols.) The composition and size of the phage DNAs are listed in Table 3. Their % G+C values ranged from 37–38, which is virtually identical to the mol % G+C values reported for serotype c, e and f strains of S. mutans (36%–38%). Heating and quick chilling of phage DNAs had no effect on subsequent mobility in agarose gels, indicating that they lacked cohesive ends.

TABLE 3

Size and composition of phage DNAs

| Phage | Tm (° C.) | % G + C | Length (kb) |
|---|---|---|---|
| M102 | 84.2 ± 1 | 38.0 | 32.1 ± 2 |
| e10 | 83.3 ± 1 | 37.3 | 33.5 ± 5 |
| f1 | 83.7 ± 1 | 37.0 | 30.9 ± 2 |

EXAMPLE 5

Analysis of Phage DNA

Characterization of phage DNAS. Each phage DNA is examined by electron microscopy (e.m.; E. Spiess and R. Lurz (1988) Meth. Microbiol. 20:293–323) both before and after denaturing and re-annealing to determine whether they (a) are circular or linear, (b) have cohesive ends and (c) consist of unique or permuted sequences (the latter being evidenced by circles larger than unit length genomes). The presence, and extent of terminal redundancy is also determined by E.M., by digesting for various time periods with exonuclease III and then observing circular molecules after renaturation. Single-stranded ends are detected by comparing the mobility of end fragments before and after S1 nuclease digestion. To detect covalently attached proteins, restriction fragment sizes are compared between untreated DNAs (extracted with phenol alone) and DNAs treated with Proteinase K. To determine whether any proteins found are attached to the 5' or the 3' ends of the DNA, gel mobilities are determined before and after treatment with exonuclease III and λ-exonuclease (A. Romero, R. Lopez, R. Lurz and P. Garcia (1990) J. Virol 64:5149–5155).

All phage DNAs are restricted with a battery of restriction enzymes, preferably EcoRI, BamHI and HindIII, and the resulting patterns (and fragment sizes) compared. They are mapped, insofar as possible by the classical techniques of mixed, partial and sequential digests. To locate sites which occur with high frequency or which cannot be unambiguously mapped, fragments are end-labeled using the standard partial digest approach, by biotinylating known end fragments and using them as probes to order the sites by hybridization with Southern blots of partial digests. This method confirms whether the phage genomes have permuted or unique sequences and terminal redundancy (or terminal repeats, if their genomes are not circularly permuted).

The SfiI linker mapping system (Promega) is one way to map the phage DNAs in more detail. This method involves subcloning into λGEM-11, 12 (EMBL3, 4 derivatives), excising the fragment with SfiI, partially digesting with test enzymes and then hybridizing Southern blots of agarose gels with oligo probes specific for each uniquely constructed SfiI terminus (Promega).

Phage DNA relationships. Each DNA is restricted with an appropriate enzyme(s) to cut each phage DNA into small fragments, and is electrophoresed in agarose gels, depurinated with 0.25 N HCl, denatured with alkali, neutralized and transferred to filters by the Southern blot procedure. The blots are hybridized with in vitro labeled, heat denatured whole phage DNAs to determine which fragments of each phage carry sequences in common with the labeled phages. Probes for specific genes (or regions of each genome) can also be used on similar blots to reveal more detailed relationships than can be obtained using whole phage DNA probes. In general, these probe sequences are isolated from recombinant phages/plasmids by using the appropriate restriction enzymes. The desired sequences are separated by excising bands from preparative-scale low melting point agarose gels, purified with GENECLEAN (Bio 101) or QIAGEN and, after heat-denaturing, labeled in vitro with biotin. The latter is accomplished by the photobiotin technique (BRL) or by incorporating biotin-7-dATP in a standard nick translation system (BRL). Hybridized probes are detected by the streptavidin-alkaline phosphatase Blu-GENE® system (BRL).

Heteroduplex mapping (by electron microscopy) is also conducted by the method of (A. Romero, R. Lopez, R. Lurz and P. Garcia (1990) *J. Virol* 65:5149–5155; E. Spiess and R. Lurz (1988) *Meth. Microbiol* 20:293–323), to determine specific regions of non-homology between and deletions in each of the phages.

These methods are used to detect deletions, gene rearrangements and other DNA sequence differences among the phages, and the existence of unique sequences, which may be correlated with host range specificity.

EXAMPLE 6

Hybridization of Phage DNAs with Biotinylated Phage Probes

The results obtained by hybridizing each phage DNA with the two biotinylated whole phage DNA probes are listed in Table 4. Both probe DNAs hybridized with all three phages, indicating that they shared some common sequences. Neither probe hybridized to any host strain tested nor to media, saliva, or unrelated phage DNAs, providing the membranes were treated with proteinase K, which was necessary to eliminate background reactions.

TABLE 4

Hybridization of phage DNAs

| | Labeled Probe DNA | |
|---|---|---|
| Test Phage[a] | M102 | e10 |
| N3 | 0 | 0 |
| A1 | 0 | 0 |
| M102 | + | + |
| e10 | + | + |
| f1 | + | + |

[a]N3 and A1 are phages of *A. naeslundii* and *A. viscosus*, respectively.

Figure 5:
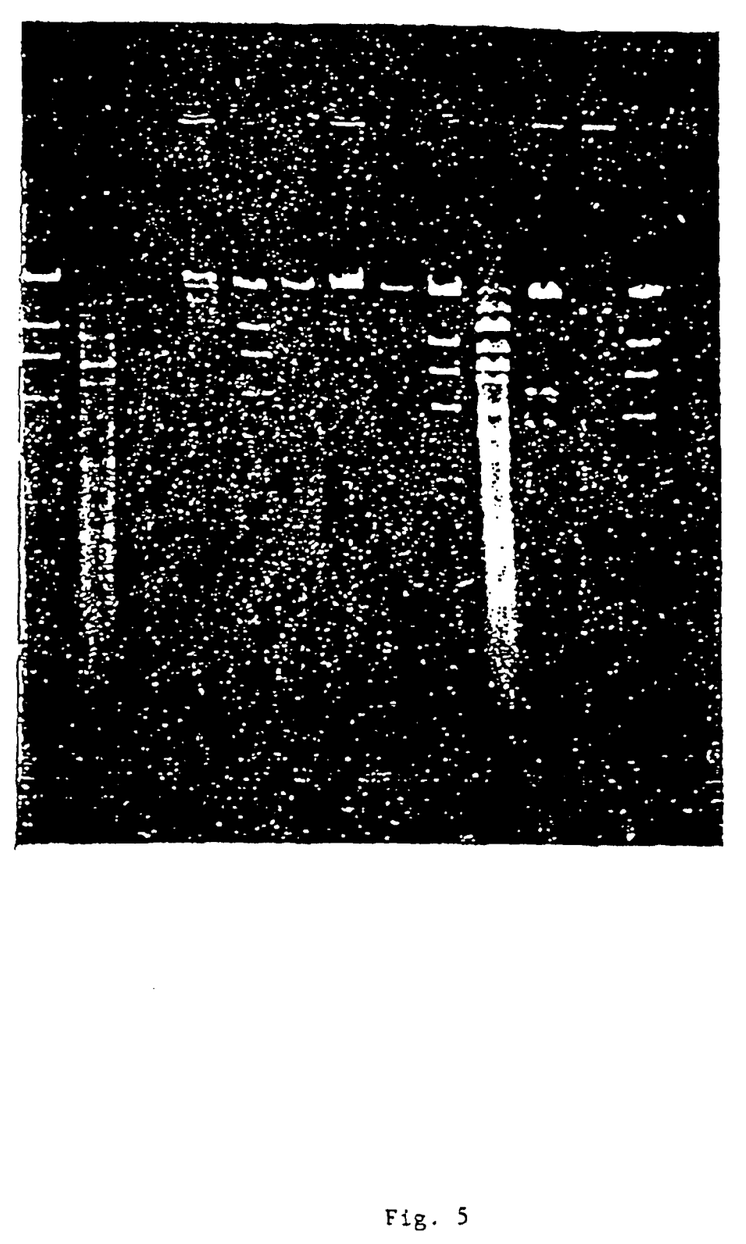
FIG. 5 shows restriction digests of *S. mutans* phage DNAs with HindIII and EcoRI. Lanes: (1), (5), (9), and (13), Lambda HindIII fragments (standards); (2), (3), (4), HindIII restriction digests of e10, f1 and M102, respectively; (10), (11), (12), EcoRI restriction digests of e10, f1 and M102 DNAS, respectively; (6), (7) and (8), whole phage DNAs.
Figure 6:
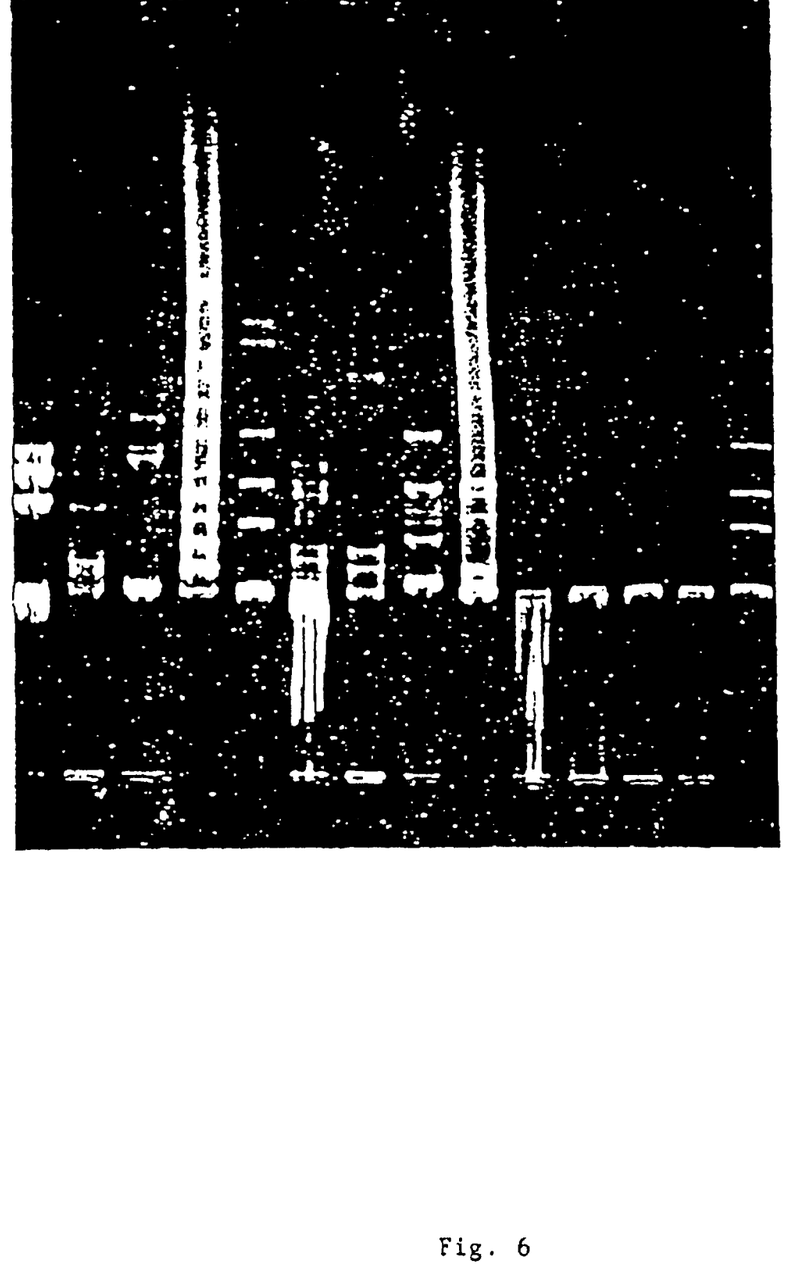
FIG. 6 shows restriction digest of *s. mutans* phage DNAs with BamHI and EcoRI. Lanes: (1) and (10), lambda HindIII fragments (standards); (2), (3), (4), (5), whole phage DNAs of e10, f1, M102 and lambda, respectively; (6), (7), (8), (9), BamHI restriction digests of e10, f1, M102, and lambda DNAs, respectively; (11), (12), (13), (14), EcoRI restriction digests of e10, f1, M102, and lambda DNAS, respectively.

Restricting each phage DNA with EcoRI, BamHI and HindIII produced fragment patterns unique to each phage (FIGS. 5 and 6). HaeIII cleaved each DNA into many fragments. The total length of each phage DNA, calculated from the size of fragments generated by each restriction enzyme, varied slightly among the phages (Table 3), but each appeared to be double stranded, linear and did not appear to have sticky ends. Whether the phage DNAs are terminally redundant or circularly permuted, is not known. Common bands between phage M102 and e10 and between M102 and f1 were produced by BamHI. This indicates some similarities in genome organization but the otherwise unique restriction fragment patterns suggests that these three phages have evolved separately, the differences presumably being a reflection of accumulated mutations and gene rearrangements.

EXAMPLE 7

Detection/Assay of Phage Lysozymes (Lysins)

Figure 7:
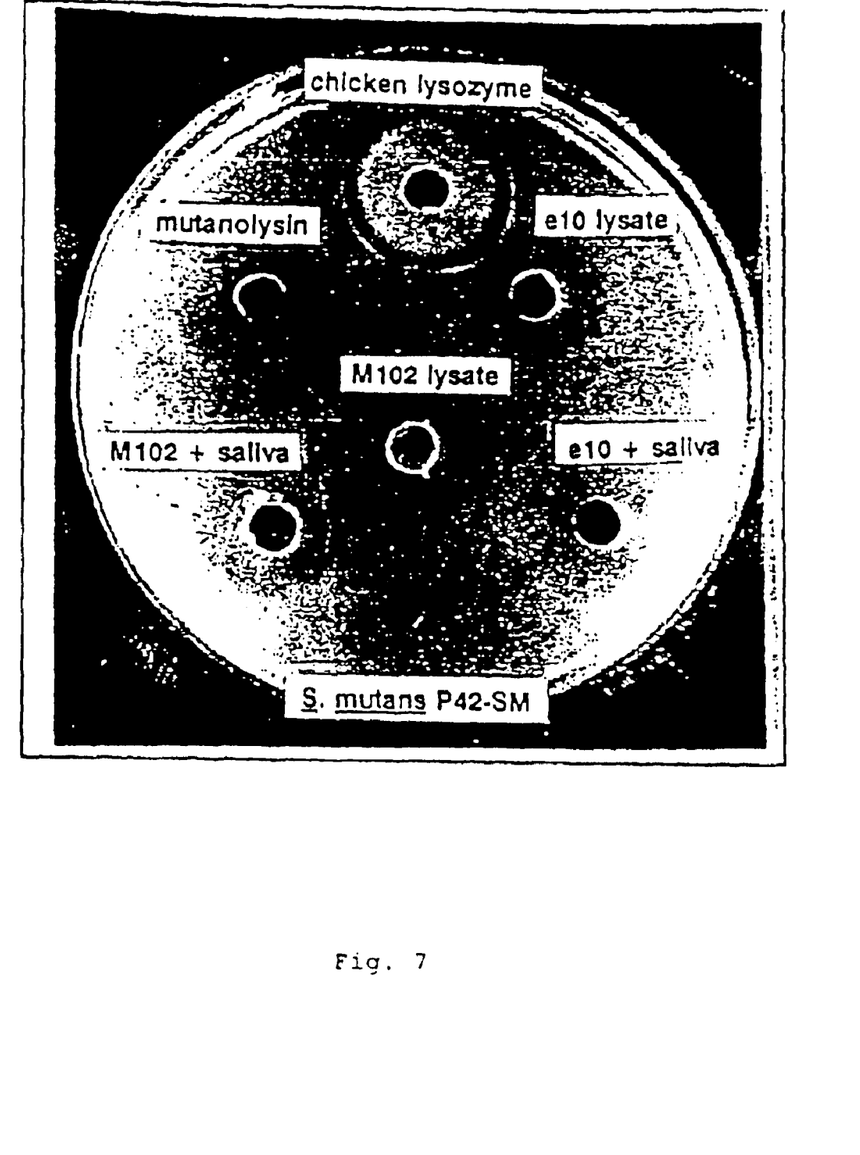
FIG. 7 shows lysoplate detection of lysozome-like activity against S. *mutans* strain P42-SM (serotype c), of chicken egg white lysozyme, mutanolysin, undiluted lysates of phages M102 and e10, and phage lysates diluted with an equal volume of freshly collected, unstimulated saliva.

Lysoplate detection of lysozyme-like activity against *S. mutans* strain P42-SM (serotype c) was studied. Cells were grown to stationary phase in Trypticase Soy Broth supplemented with 5 g/l yeast extract and 10 mM L-threonine, washed 2× in Tris-EDTA (10 mM Tris-1 mM EDTA, pH 8.0), once in dH$_2$O and then re-suspended in ¼ original vol of 0.85% saline. Ten ml of concentrated cells (4×) were mixed with 10 ml of 2% agarose-0.85% saline-10 mM phosphate buffer, pH 7.0, at 45° and poured into a petri dish. After solidifying, holes were cut in the plate with a cork borer and the wells filled with ~150 µl of the following enzyme solutions or phage lysates, as indicated: chicken egg white lysozyme (Sigma, ca. 10 mg/ml); mutanolysin (sigma, 2 mg/ml); undiluted lysates of phages M102 and e10; and phage lysates diluted with an equal volume of freshly collected, unstimulated saliva. (Note precipitation of cells at high lysozyme concentration, FIG. 7). The saliva was added to 2 samples as a control, to see if components present might interfere with phage lysozyme action.

The high diffusibility of the active agent in each well (see FIG. 7) indicates that they are enzymes and not large phage structures, which cannot diffuse in 1% agarose to the extent observed. Lysis therefore cannot be the result of phage infection or adsorption. The lysis of washed, stationary-phase, nongrowing cells also indicates that lysis is not dependent on cell metabolism or due to an autolytic response.

EXAMPLE 8

"Lysoplate" Assay of *S. sobrinus* 6715

*S. sobrinus* 6715 was tested with the 3 phage lysates in agarose plates buffered to pH 4.4, 5.0, 6.0 and 6.8. The maximum zone of lysis (in this case with a lysate of phage f1) occurred at pH 5.0; the zones at pH 4.4 and 6.0 were slightly smaller and at pH 6.8 the lysis zone was considerably reduced in size.

EXAMPLE 9 pH Optimum of Phage Lysins

The protocol for growing and washing cells of *S. mutans* P42 is the same as described in Example 7 except that log-phase cells are used. The final concentration of agarose in the plates is reduced to 0.6% and the pH was re-adjusted after autoclaving and cooling the medium to 50° C. Representative data is given in Table 5.

TABLE 5

Size of lysis zones, in mm, caused by 3
S. mutans phage lysozymes in lysoplates containing
S. mutans P42. (Includes well diameter of 3 mm).

| pH | phage M102 | lysate e10 | f1 |
|---|---|---|---|
| 4.0 | 7 | 7 | 11 |
| 5.0 | 6 | 5 | 9 |
| 6.0 | 6 | 5 | 9 |
| 7.0 | 4 | 4 | 7 |
| 8.0 | — | — | 6 |
| 9.0 | — | — | 6 |

In some experiments pH optima of 5–6 were obtained, but clearly these enzymes are capable of working well at very low pH values. When similar plates were made with 0.1% w/v lyophilized cells of M. luteus (obtained from Sigma) and tested with chicken lysozyme, similar zone sizes were produced at a concentration of 2–5 µg/ml (using a preparation stated to contain 48,000 Units/mg) and maximum sizes were observed at pH 8–9.

EXAMPLE 10

Phage Host Ranges

The S. mutans phage host ranges, that is, host strains in which the phage can infect and replicate, are listed in Table 6. The host range of the Actinomyces phage Av-1 is limited to the MG-1 strain of A. viscosus; and phage CT4 hosts include most strains of A. viscosus and A. naeslundii. The S. mutans phage lysozymes inhibit all strains of this species, even those which they cannot infect (and phage-resistant mutants of those they can infect), but NONE of the gram-positive species listed in Table 7. The latter shows that the enzymes are uniquely different from other lysozymes, i.e., human, chicken and mutanolysin, which can attack the cell walls of most of the strains listed when special conditions are used. M. luteus is the standard strain used to assay all lysozymes.

The Actinomyces phage lysozymes are only effective against strains of A. viscosus and A. naeslundii and none of the other strains listed in Table 6 and 7.

TABLE 6

Host rang of Streptococcus mutans phages

| Species | Strain | Serotype | Plasmid | Bacteriophage[a] M102 | e10 | f1 |
|---|---|---|---|---|---|---|
| S. cricetus | AHT | a | – | – | – | – |
| S. rattus | BHT | b | – | – | – | – |
| S. mutans | P42-SM | c | – | + | – | – |
| S. mutans | 10449 | c | – | – | – | – |
| S. mutans | UA174 | c | + | + | – | – |
| S. mutans | V318 | c | + | – | – | – |
| S. mutans | UA101 | c | + | – | – | – |
| S. mutans | LM7 | e | + | – | + | – |
| S. mutans | LM7-SM | e | – | – | + | – |
| S. mutans | P4 | e | – | – | + | – |
| S. mutans | B14 | e | – | – | + | – |
| S. mutans | OMZ175-SM | f | – | – | – | + |
| S. sobrinus | 6715 | g | – | – | – | – |
| S. sobrinus | OMZ176 | d | – | – | – | – |

[a]+, sensitive to phage; –, phage resistant.

TABLE 7

List of oral and non-oral gram-positive species
which have been tested and found to be resistant to
lysis and plaque formation by all 3 S. mutans phages

| Species | Strains |
|---|---|
| Streptococcus salivarius | H$_2$ |
| Streptococcus sanguis | 10556, C104 |
| Streptococcus gordonii | 10588, 488, DL1 (Challis) |
| Streptococcus oralis | J22, 10557, H1 |
| Group H streptococci | Channon, FW227, 8684, E91/46 |
| Streptococcus SM | PK509 |
| Lactobacillus casei | 4646 |
| Actinomyces naeslundii (A. viscosus) | MG-1, T14V |
| Micrococcus luteus (M. lysodeikticus) | 4698 |
| Bacillus subtilis | W23 |
| Streptococcus aureus | 25923 |
| Streptococcus pyogenes | 19615 |

EXAMPLE 11

Experiments with Phages Isolated from other Types of Bacteria

Actinomyces phages. Studies on Actinomyces phages have yielded some data and general information which are relevant and can be applied to the present invention. First, the small, Group I phages (A. L. Delisle, J. A. Donkersloot, P. E. Kolenbrander and C. A. Tylenda (1986) Int. Congr. Microbiol., Manchester, Eng. September. 11; C. Rostkowski and A. Delisle (1989) Abstr., 89th Ann. Mtg., Amer. Soc. Microbiol., p. 343, No. Q-82; C. A. Rostkowski, (1989) M. S. Thesis. Univ. of MD at Baltimore. Jun. 8, 1989 68 pp.) have been found to have proteins attached to their DNAs. They are thus similar to the small Bacillus phages (e.g., φ29 and PZA) and to S. pneumoniae phage Cp-1. (Recently, other phages of the latter species, similar in size to S. mutans phages, have also been found to contain proteins attached to their DNAs; A. Romero, R. Lopez, R. Lurz and P. Garcia (1990) J. Virol. 64:5149–5155). A preliminary hybridization experiment in fact showed weak homology between Φ29 and A. viscosus Av-1 phage DNAs.

Bacillus phages. It turns out that the phage-encoded lysozymes of the small Bacillus phages (M. S. Saedi, K. J. Garvey and J. Ito (1987) Proc. Natl. Acad. Sci., USA 84:955–958) are closely related to the phage-encoded lysozymes of P22 of Salmonella typhimurium and T4 of E. coli, each having a nearly identical sequence in their N-terminal regions. They differ substantially in their carboxy terminal regions. More recently, the phage-encoded lysozymes of two Lactococcus phages have been sequenced, and they also have strong amino acid homologies with the other lysozymes (C. Shearman, H. Underwood, K. Jurg and M. Gasson (1989) Mol. Gen. Genet. 218:214–221; A. Trautwetter, P. Ritzenthaler, T. Alatossava and M. Mata-Gilsinger (1986) J. Virol. 59:551–555). Thus, phage-encoded lysozymes from a wide variety of genera all appear to be related, at least near the active site of the enzyme. The sequence of phage Cp-1 lysin differs in this region, but this is to be expected since this enzyme is specific for the unique, choline-containing cell walls of the pneumococcus (E. Garcia, J. L. Garcia, P. Garcia, A. Arraras, J. M. Sanchez-Puelles and R. Lopez (1988) Proc. Nat'l. Acad. Sci. 85:914–918; J. L. Garcia, E. Garcia, A. Arraras, P. Garcia, C. Ronda and R. Lopez (1987) J. Viol. 61:2573–2580).

EXAMPLE 12

Identification of Related Phase Sequences

By comparing the DNA sequences of the above phage lysozymes, and taking into account the codon bias observed in the known sequences of 2 cloned *S. mutans* genes, the following 23-mer oligonucleotide probe (SEQ. ID NO:1) was designed, which is ambiguous in only one position (T vs.,C), that should hybridize to *S. mutans* phage lysosyme genes if the above relationships apply to this species:

By making appropriate base changes and varying hybridization stringency conditions, such probes can be used to identify even more distantly related sequences. It should also be noted that several restriction sites occur within the phage lysozyme sequences examined above (including EcoRI); this information is used in selecting enzymes for cloning these genes intact.

EXAMPLE 13

Cloning of Phage Genes

Since introns do not occur in any known dsDNA phages (with the sole exception of T4), determining the nucleotide sequence of a phage gene reveals the true amino acid sequence of its corresponding protein. The DNA sequence upstream of the first codon also provides information on how the expression of the gene may be regulated since this region codes for the ribosomal binding sites, operators and promoters that are used for expression.

Small, random fragments of phage DNAs are cloned into the plasmid vectors pUC19 and pBluescript, by standard procedures (J. Sambrook, E. F. Fritsch and T. Maniatis (1989) A Laboratory Manual, 2nd ed. Cold Spring Harbor Lab. Press, N.Y. 3 vols.). Since phage vectors do not rely on host viability (and because they also cause release of intracellular constituents, thereby facilitating detection of foreign proteins) fragments are also cloned in λgt10.

If the phage lysozymes prove to be lethal when expressed in *E. coli*, other vectors whose expression of foreign inserts can be controlled (e.g., by a heat-sensitive repressor) are used to isolate these genes without relying on expression from their own associated promoters. The prokaryotic expression vector pNH18a (Stratagene), for example, enables lethal genes to be expressed when desired by simply heat pulsing (to switch its promoter to the ON position) and adding IPTG (to de-repress its plac promoter).

Preparation of DNA fragments. Partial digests of each phage DNA are made with HaeIII, a frequent 4-base cutter that generates blunt end fragments or Sau3AI which generates BamHI-compatible ends. Conditions are varied (time, enzyme concentration) to maximize production of appropriate-size fragments (5–10 kb) which are then fractionated by sucrose density gradient centrifugation (J. Sambrook, E. F. Fritsch and T. Maniatis (1989) A Laboratory Manual, 2nd ed. Cold Spring Harbor Lab. Press, N.Y. 3 vols.). These are purified by phenol extraction and ethanol precipitation and, without further treatment, used to clone in both types of vectors.

Plasmid cloning. Plasmids are cut with BamHI (or with EcoRI and then blunt-ended) and dephosphorylated with calf intestinal alkaline phosphatase (CIAP; J. Sambrook, E. F. Fritsch and T. Maniatis (1989) A Laboratory Manual, 2nd ed. Cold Spring Harbor Lab. Press, N.Y. 3 vols.). After removing the CIAP, the vector and fragments are mixed in various ratios, ligated with the appropriate amount of T4 ligase and then transformed (or electroporated) into *E. coli* DH5α to select transformants and detect recombinants.

Phase cloning. λgt10 is purchased as purified cos-ligated, EcoRI-cut, dephosphorylated molecules (BRL). The 4 base-pair 5' overhangs are filled in, to produce blunt ends, by treatment with the Klenow-fragment of DNA polymerase and DATP and dTTP (J. Sambrook, E. F. Fritsch and T. Maniatis (1989) A Laboratory Manual, 2nd ed. Cold Spring Harbor Lab. Press, N.Y. 3 vols.). After phenol extracting and precipitating, the vector and fragment DNAs are mixed in the appropriate ratios and blunt-end ligated. The resulting concatamers are packaged in vitro (BRL Packagene system) and plated on *E. coli* C600 hfl A150 to yield recombinant (clear) plaques. An alternative procedure is to use Sau3AI-partially digested phage DNA and λgt10 arms modified by ligating EcoRI-BamHI adapter, to change the overhangs to Sau3AI-compatible BamHI ends.

Detection of recombinants. Plasmid transformants are plated on LB agar containing ampicillin, to select for cells which acquire a plasmid, and IPTG+X-gal. The latter two substances will result in blue colonies if a complementation occurs between the lacZΔ 15 peptide of the host and the ΔlacZ peptide fragment of the vector, whereas inserts in the vector result in colorless colonies. The latter are picked and screened for the desired genes.

In the λgt10 cloning system, the hf1 host is so efficiently lysogenized by the wild type phage that most of the resulting plaques are due to interruptions in the cI gene, which give rise to clear plaques, and are therefore mainly recombinant phages. These are screened for the presence of the desired genes or gene products.

Screening recombinants. Colony and plaque blots are made to detect the presence of probe-related sequences by standard hybridization methods, using the phage lysozyme probe described above.

To detect enzymatically active proteins, several methods are employed. For phage lysozymes, colonies/plaques are overlaid with 3–5 ml of top agarose seeded with 10% (v/v) of a 50-fold concentrated suspension of washed cells of the appropriate *S. mutans* host (C. Shearman, H. Underwood, K. Jurg and M. Gasson (1989) *Mol. Gen. Genet.* 218:214–221). Plates are incubated and observed for zones of clearing in the lawn above the colonies/plaques. As an ernative detection method, top agar seeded with 0.1–0.2 ml of fresh host cells can be overlaid on top of colonies/plaques and then incubated (penicillinase is added for the plasmid-containing recombinants since they are grown in the presence of ampicillin). As the lawn develops during incubation, areas of lysis develop over lysozyme-producing recombinants.

A third method to detect expression of phage lysozyme in *E. coli* recombinants involves making individual top agar overlays of each culture and spotting with various dilutions of a bacteriophage T4e mutant (lysozyme gene deletion), incubating the plate and then observing for the presence of T4 plaques. Plaque formation indicates complementation of the missing T4 lysozyme gene product by the phage lysozyme gene expressed in the recombinant.

If the lysozyme detection methods do not work satisfactorily, colony/plaque blots are probed with phage lysozyme-specific oligonucleotides. These probes are synthesized on a DNA synthesizer. An amide linker is added to the last 5' base and after purifying on an ABS oligo purification cartridge, alkaline phosphatase is directly attached to the linker (GIBCO/BRL ACES system). Hybridized probe is detected by the ACES chemiluminescent system (BRL). Specificity and optimum hybridization conditions are determined with the appropriate phage DNAs to ensure that the sequence is in fact present in the phage genome. Other alternative screening procedures include simply assaying recombinant cell extracts for lysozyme-like activity or purifying the enzyme from a broth lysate, preparing antiserum to it and then using this antiserum to detect antibody-reactive proteins in colony/plaque blots.

To detect EPS depolymerases, agar overlays containing Blue dextran (Sigma) are made on top of recombinant colonies and observed for halos (J. F. Barrett, T. A. Barrett and R. Curtiss III (1987) Infect. Immun. 55:792–802.) More specific depolymerases and enzymes active against $\alpha 1 \rightarrow 3$ branched polymers (mutans) may be detected with EPSs isolated from sucrose-grown cultures of different serotype strains of S. mutans (M. Freedman, D. Birked and K. Granath (1978) Infect. Immun. 21:17–27), by flooding overlays of EPS-containing top agar with ethanol to observe clear zones in the opaque background caused by precipitation of undegraded polysaccharides.

It should be pointed out that, if the cell wall-lytic enzymes encoded by these phages do not turn out to be true lysozymes (i.e., muramidases) and are therefore unrelated to other known phage lysozymes, their genes can still be isolated since the above screening methods will detect such enzymes as long as they cause visible lysis or growth inhibition of host cells.

Sequencing. The isolated phage gene (cloned as above) are sequenced by the dideoxy technique, utilizing fluorescent ddNTPs, in an Applied Biosystems automated sequencer. If the genes prove to be of manageable size they are sequenced by subcloning into an M13 sequencing vector or by using the pBluescript vector itself. The later is used to generate ss DNA phage for sequencing since it contains the f1 origin of replication and ssDNA phage progeny are produced from it by infecting the host with the appropriate helper phage. This allows standard M13 sequencing methods to be used. If the cloned sequences are too long to use this approach, shorter fragments are subcloned by using appropriate restriction enzymes or by preparing a series of deletion fragments covering the region of interest (J. Sambrook, E. F. Fritsch and T. Maniatis (1989) A Laboratory Manual, 2nd ed. Cold Spring Harbor Lab. Press, N.Y. 3 vols.). Alternatively, primers are synthesized, as sequencing data is obtained, to extend into more distant regions. Sequencing systems include the Sequenase system (U.S. Biochem. Corp.) and Taq polymerase sequencing PCR techniques. These techniques obviate the need to subclone fragments of interest.

EXAMPLE 14

Characterization of Dextranases (S. mutans phages)

A. Detection of dextranase in phase lysates. The Blue dextran (Sigma)-containing medium dex 10 was found to be the most sensitive dextranase detection medium (Ref: Donkersloot, J. A. and R. J. Harr. 1979. More sensitive test agar for detection of dextranase-producing oral streptococci and identification of two glucan synthesis-defective dextranase mutants of Streptococcus mutans 6715. J. Clin. Microbiol. 10:919–922). Colonies of each phage host strain (P42, OMZ 175 and LM7) grown on this medium produced decolorized zones, indicating dextranase activity. When 5 $\mu l$ of sterile filtered phage lysates (M102, e10 and f1) were spotted onto this medium dextranase activity was evident after overnight incubation at 37° C. (no bacterial growth).

pH Optimum of lysate dextranases. To determine the approximate pH optima of the dextranase in phage lysates, 10 ml of autoclaved 0.85% NaCl containing 0.25% blue dextran and 0.6% agarose (buffered to various pHs with 0.010 M phosphate) were pipetted into 5 cm petri dishes, allowed to solidify and then wells were cut from the agar with a 5 mm diameter cork borer. The wells were filled with 100–125 $\mu l$ of sterile filtered phage lysate and the plates were incubated overnight at 37° C. The size of the resulting clear (dextranase) zones, in mm, are given in Table 8.

TABLE 8

Dextranas activity in phage lysates.

| Phage Lysate | pH | | | |
|---|---|---|---|---|
| | 4.4 | 5.0 | 6.0 | 6.8 |
| M102 | 8 | 8 | 7.5 | 7.5 (weak) |
| e10 | 8.5 | 10 | 9.5 | 9.0 |
| f1 | 10 | 11 | 10 | 8.5 |

The data suggest pH optima of 5–6, with significant activity at 4.4 (the lowest tested), indicating these enzymes would be active in highly acidic, caries-active dental plaque.

Association of dextranase with phage virions. The three phages were sedimented by centrifuging sterile filtered lysates for 2 hours at 48,000×g. The phage pellets, but not the supernatant fluids, contained dextranase activity when tested by the above described agarose plate method (at pH 5.0 and 6.0). As this technique does not rule out the possibility of contamination with small amounts of host dextranase, the phage were purified by equilibrium CsCl density gradient centrifugation. Seven grams of CsCl were added to each 10 ml of filtered lysate and the resulting mixtures were centrifuged at 30,000 rpm for 65 hours in a Beckman SW 41 rotor. Three-drop fractions were collected from the bottom of each tube and tested for dextranase activity by placing 100 $\mu l$ into separate wells of pH 5.0 agarose-blue dextran plates (as above). In each case the two fraction containing the purified, whole phage band (density= 1.40 g/cc) had dextranase activity. Proteins (enzymes) have a much lower buoyant density than whole phage virions (which contain DNA) so contamination of this band with host dextranase is extremely unlikely. The data therefore suggest that the phages have a dextranase-like enzyme as part of their tail structure.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

What is claimed is:

1. A method for preventing spoilage of food items from bacteria, said method comprising adding to said food items an effective amount of at least one lytic enzyme genetically coded for by a specific bacteriophage specific for a specific gram positive bacteria causing said spoilage of said food items, wherein said at least one lytic enzyme is specific for and has the ability to digest a cell wall of one of said bacteria and is coded for by the same said bacteriophage capable of infecting said bacteria being digested.

* * * * *